United States Patent [19]
Ito et al.

[11] Patent Number: 5,288,387
[45] Date of Patent: Feb. 22, 1994

[54] APPARATUS FOR MAINTAINING THE ACTIVITY OF AN ENZYME ELECTRODE

[75] Inventors: Takayuki Ito; Hideo Katayama, both of Tsukuba, Japan

[73] Assignee: Daikin Industries, Ltd., Japan

[21] Appl. No.: 712,669

[22] Filed: Jun. 10, 1991

[30] Foreign Application Priority Data

Jun. 12, 1990 [JP] Japan ............................ 2-154527

[51] Int. Cl.$^5$ .................. G01N 27/327; G01N 27/38
[52] U.S. Cl. ................... 204/402; 204/153.12; 204/153.17; 204/403; 204/415
[58] Field of Search ............... 204/400, 402, 403, 415

[56] References Cited

U.S. PATENT DOCUMENTS

| | | | |
|---|---|---|---|
| 3,616,412 | 10/1971 | Gnage | 204/402 |
| 4,057,478 | 11/1977 | Bruckenstein et al. | 204/415 |
| 4,477,314 | 10/1984 | Richter et al. | 204/402 |
| 4,897,162 | 1/1990 | Lewandowski et al. | 204/402 |
| 4,950,378 | 8/1990 | Nagata | 204/415 |

FOREIGN PATENT DOCUMENTS

| | | | |
|---|---|---|---|
| 7060255 | 4/1982 | Japan | 204/402 |
| 1531761 | 11/1978 | United Kingdom | 204/402 |

*Primary Examiner*—T. Tung
*Attorney, Agent, or Firm*—Beveridge, DeGrandi, Weilacher & Young

[57] ABSTRACT

A concentration measuring apparatus includes an enzyme electrode which accelerates an oxidation reaction or a reduction reaction of a test substance in a liquid and outputs an electrical signal corresponding to a quantity of the test substance therefrom due to the reaction. The enzyme electrode is supplied with a reviving voltage for removing interfering substances on the enzyme electrode not only prior to concentration measuring but also according to a predetermined time interval. The reviving voltage has a polarity which is the reverse of the voltage used for concentration measurement.

3 Claims, 4 Drawing Sheets

APPARATUS FOR MAINTAINING THE ACTIVITY OF AN ENZYME ELECTRODE

BACKGROUND OF THE INVENTION

The present invention relates to methods and apparatus for maintaining the activity of an enzyme electrode, and more particularly to methods and apparatus for maintaining an enzyme electrode in activated condition while it is provided in a concentration measuring apparatus for measuring the concentration of a test substance in a test solution based upon an oxidation reaction or a reduction reaction of the test substance in a surfacial region of the enzyme electrode.

It is known that a physiologically active substance is capable of selectively detecting a very complicated organic compound, a protein or the like with high sensitivity. With attention directed to this characteristic, research has been made in various biosensors.

A typical biosensor (hereinafter referred to as an enzyme electrode) having an electrode unit and a physiologically active substance fixed thereon is proposed. The enzyme electrode is used for detecting the existence of a test substance, the relative or active quantity of the test substance and the like based on an electrical signal output from the electrode unit corresponding to the biological reaction of the test substance, under the condition that a predetermined forward bias is applied to the electrode unit. For example, the electrode unit generally has a working electrode made of platinum having high activity and a counter electrode made of silver having a high stability. When glucose as the test substance in the test solution is to be measured, the enzyme electrode generally has an arrangement wherein a hydrogen peroxide penetration membrane, an enzyme-immobilized membrane including glucose oxidase as a physiologically active substance, and a diffusions-limiting membrane are laminated in this order. When the enzyme electrode is employed, glucose is oxidized in the presence of glucose oxidase so as to generate gluconic acid and hydrogen peroxide. Then the generated hydrogen peroxide reaches the surface of the electrode unit through a hydrogen peroxide penetration membrane. The electrode unit outputs an electrical signal corresponding to the quantity of hydrogen peroxide that reaches it. The relative or active quantity of glucose in test solution is detected based on the electrical signal. In this case, when the activity of the platinum electrode is lowered, the level of the electrical signal is remarkably lowered. When the platinum electrode is kept as it is for a long time period, an oxidized layer which interferes with electrical signals is formed on the platinum electrode so as to lower the activity of the platinum electrode.

The same disadvantages as above arise for an enzyme electrode which is used for measuring a concentration of a test substance other than glucose.

It is proposed that a reviving voltage, which has a polarity which is reverse with respect to the polarity of a voltage for concentration measurement, is applied to the electrode unit so as to remove the oxidized layer on the electrode unit thereby to enable a concentration measurement with high sensitivity.

A disadvantage arises in that the oxidized layer cannot be perfectly removed even when the reviving voltage is applied to the electrode unit due to an increase in the thickness of the oxidized layer on the electrode unit. The increase in thickness is determined based on lengthening of the time interval between concentration measurements. In this case, when concentration measurements are carried out with a relatively short time interval, the thickness of the oxidized layer which remains after the revising voltage is applied to the electrode unit is gradually decreased at every concentration measurement so as to improve the activity of the electrode unit. As a result, drift appears in the output electrical signals so as to lower the accuracy in the concentration measurement (see FIG. 9).

To reduce the disadvantage above-mentioned, it is necessary that the reviving voltage is raised or the time period for applying the reviving voltage is lengthened. This causes an increase in the quantity of the generated substance, i.e. hydrogen, hydrogen ions and the like, which is generated on the electrode unit by applying the reviving voltage so as to increase the diffusion current which is caused by the generated substance generated. As a result, the necessary time period for the decreasing of the diffusion current to a predetermined threshold value is reduced. The disadvantage arises that the time period is lengthened between performing the reviving operation for the electrode unit to when it is possible to start a measuring operation for a test substance.

The same disadvantages as above arise for an enzyme electrode having a reference electrode in addition to the working electrode and the counter electrode.

SUMMARY OF THE INVENTION

It is an object of the present invention to maintain a high degree of concentration measuring accuracy despite the time interval Of concentration measurements.

It is another object of the present invention to shorten the time period between performing a reviving operation for an electrode unit to when it is possible to start a measuring operation for a test substance.

This present invention applies a predetermined reviving voltage to an electrode unit for reviving an enzyme electrode unit which includes the electrode unit at every predetermined time interval and applies a predetermined reviving voltage to the electrode unit before a measuring operation is carried out.

In this maintaining method, when a concentration measuring operation has not been carried out for a long time period, the electrode unit is supplied with the reviving voltage at every time period for activating the enzyme electrode so as to prevent the oxydized layer on the electrode unit from increasing in thickness to too great on extent. As a result, the enzyme electrode is maintained with its activity not reduced to too great an extend. The electrode unit is also supplied with the reviving voltage before the concentration measuring operation is carried out so as to revive the activity of the enzyme electrode sufficiently and to perform a concentration measurement accurately even when the reviving voltage is not too high or the reviving voltage is not applied for too long a time period.

In this case, application of the reviving voltage at every predetermined time interval may be taken into consideration before the concentration measuring operation is carried out.

It is preferred that the electrical signal is compared with the predetermined threshold value so as to judge whether or not the enzyme electrode is in error after the reviving voltage, at every predetermined time interval, is applied to the electrode unit.

In this case, a concentration measuring operation using the enzyme electrode when it is in an erroneous condition is reliably prevented because the enzyme electrode is judged as to whether or not it is in an error condition based on the electrical signal output from the electrode unit due to the application of the reviving voltage at every predetermined time interval, which voltage application does not depend on the concentration measuring operation.

This present invention comprises;

reviving power source means for applying a reviving voltage to an enzyme electrode for activating the enzyme electrode;

first connection means for interconnecting the reviving power source means and the enzyme electrode at every predetermined time interval; and second connection means for interconnecting the reviving power source means and the enzyme electrode before a concentration measuring operation is carried out.

In this maintaining apparatus, when the concentration measuring operation is not carried out for a long time period, the enzyme electrode is supplied with the reviving voltage by the reviving power source means and the first connection means at every time period for activating the enzyme electrode so as to prevent an oxidized layer on the electrode unit from increasing in thickness to too great an extend. As a result, the enzyme electrode is maintained with its activity not reduced to too great an extent. The enzyme electrode is also supplied with the reviving voltage by the reviving power source means and the second connection means before the concentration measuring operation is carried out so as to revive the activity of the enzyme electrode sufficiently and to perform a concentration measurement accurately even when the reviving voltage for too long time period.

In this case, the first connection means may interconnect the reviving power source means and the enzyme electrode after a predetermined time period has passed from the interconnection of the reviving power source means and the enzyme electrode by the first or second connection means. The first connection means may interconnect the reviving power source means and the enzyme electrode after a predetermined time period from the interconnection of the reviving power source means and the enzyme electrode by only the first connection means.

It is preferred that a judging means is further included for comparing the electrical signal output from the enzyme electrode and a predetermined threshold value and judging whether or not the enzyme electrode is in an error condition based on the comparison result corresponding to application of the reviving voltage to the enzyme electrode by the first connection means.

In this case, a concentration measuring operation which uses the enzyme electrode while it is in error is reliably prevented because the enzyme electrode is judged whether or not it is in an error condition based on the electrical signal output from the electrode unit due to the application of the reviving voltage by the first connection means at every predetermined time interval, which voltage application does not depend on the concentration measuring operation.

These and other objects, features and advantages of the present invention will be more readily understood upon consideration of the present invention, taken in conjunction with the accompanying drawings.

DETAILED DESCRIPTION OF THE PREFERRED EMBODIMENTS

Figure 1:
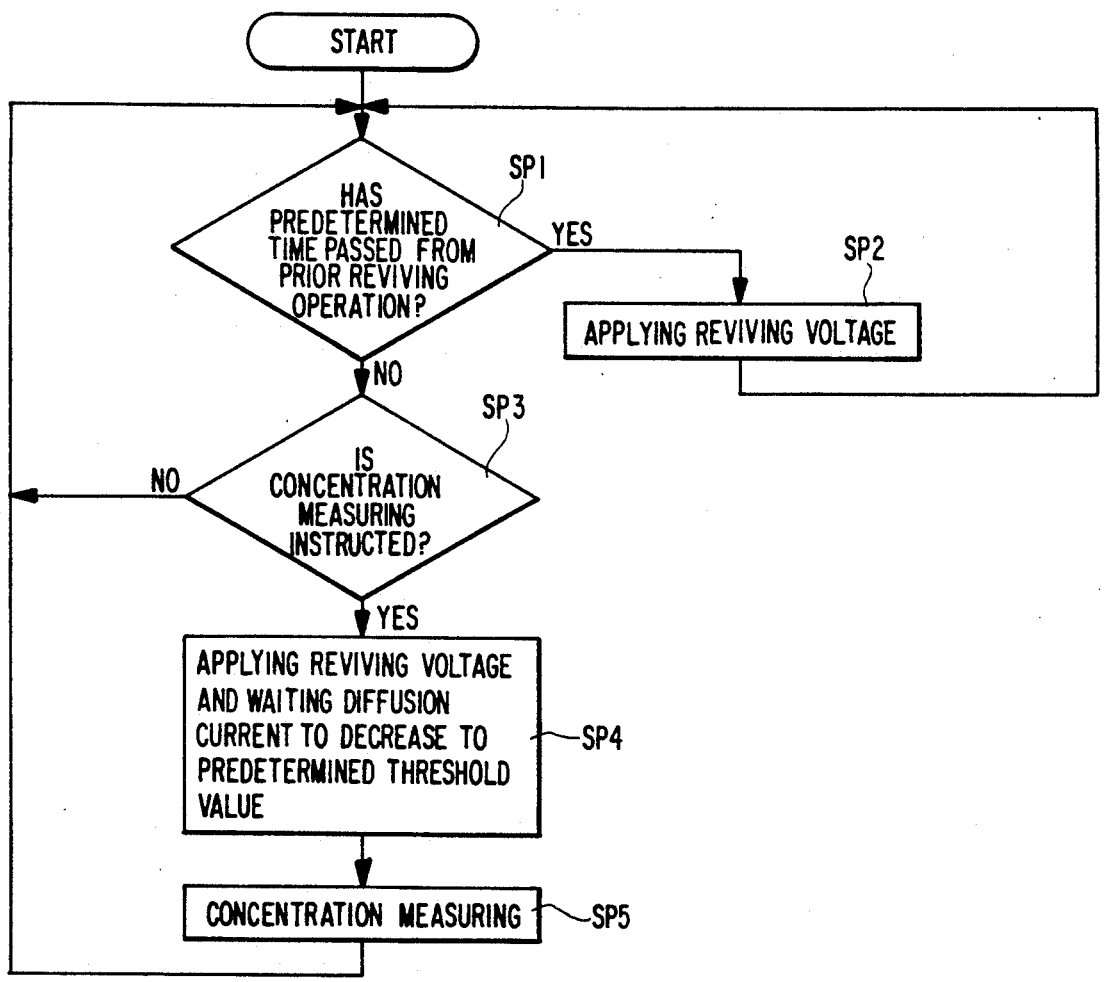
FIG. 1 is a flowchart of an activity maintaining method in accordance with a first method embodiment of the present invention.

FIG. 1 is a flowchart of an activity maintaining method in accordance with a first method embodiment of the present invention.

In step SP1, it is judged whether or not a predetermined time period T (refer to FIG. 2) has passed. When it is judged in step SP1 that the time period T has passed, a reviving voltage is applied to an enzyme electrode in step SP2 so as to revive the activity of the enzyme electrode. The reviving voltage is reversed in polarity with respect to a voltage applied to the enzyme electrode for measurement. On the contrary, when it is judged that the time period T has not passed in step SP1, it is judged whether or not concentration measuring of a test substance in a test solution is instructed in step SP3. When it is judged in step SP3 that concentration measuring is indicated, a reviving voltage is applied to an enzyme electrode in step SP4 so as to revive the activity of the enzyme electrode and to await decrease of the diffusion current to a predetermined threshold value. Then, in step SP5, a concentration measuring operation is carried out. After the processing in step SP2 or the processing in step 5 is performed, the judgement in step SP1 is carried out again. Otherwise, when it is judged in step SP3 that concentration measuring is not indicated, the judgement in step SP1 is also carried out again.

Figure 2:
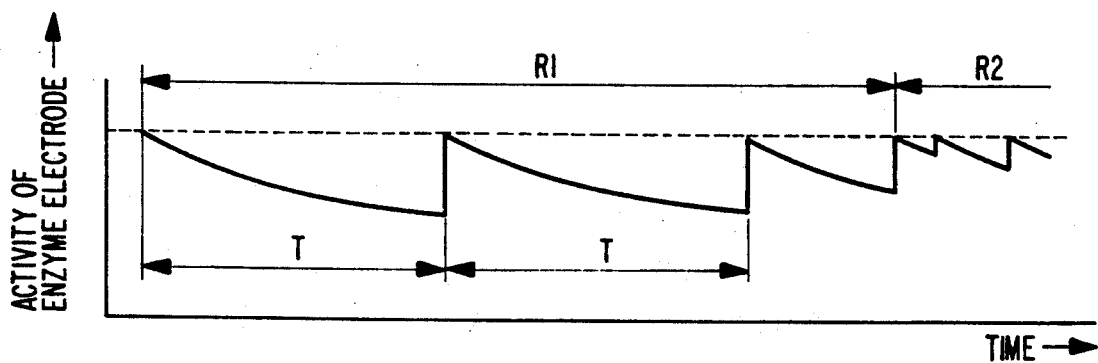
FIG. 2 is a diagram showing variations of the activity of an enzyme electrode.

As is apparent from the foregoing, the reviving voltage is applied to the enzyme electrode so as to revive activity of the enzyme electrode at every predetermined time interval T which is indicated in a region R1 in FIG. 2, even when a concentration measuring operation is not carried Out for a long time period. Reviving voltage is also applied to the enzyme electrode when concentration measuring is indicated at an arbitrary timing (refer to region R2 in FIG. 2) so as to revive the activity of the enzyme electrode sufficiently and to measure the concentration of a test substance in a test solution with high accuracy. The activity of the enzyme electrode which is used for concentration measuring is maintained constant so as to perform concentration measuring with high accuracy even when concentration measuring is repeated by a short time period for several times.

Figure 3:
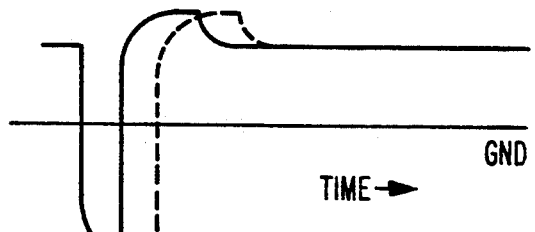
FIG. 3 is a diagram showing a reviving voltage for reviving the enzyme electrode.
Figure 4:
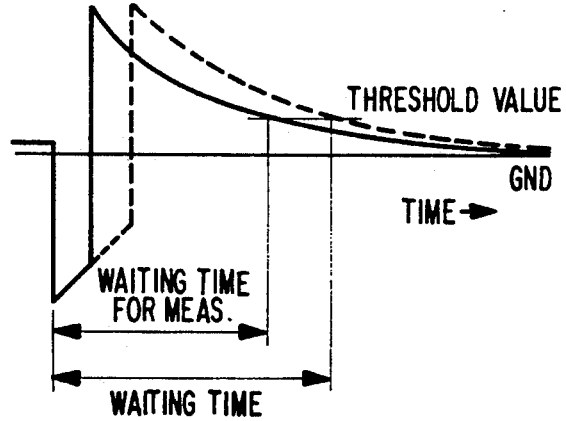
FIG. 4 is a diagram showing a current output from the enzyme electrode when a reviving operation is carried out.

Furthermore, the thickness of an oxidized layer which is to be removed by the reviving operation can be determined to be smaller than a predetermined thickness. A time period for applying a reviving voltage to the enzyme electrode can be remarkably shortened as is shown by a solid line in FIG. 3 when the reviving voltage is not varied. As a result, output current output from the enzyme electrode decreases to a predetermined threshold value within a short time period as is shown by a solid line in FIG. 4. Dotted lines in FIGS. 3 and 4 show a case in which a reviving operation is carried out only during a short time period prior to concentration measuring. As is apparent from the foregoing, the time period for awaiting concentration measuring between performing a reviving operation for the enzyme electrode to when it is possible to start a measuring operation for a test substance is reduced. Specifically, the time period for awaiting concentration measuring can be shortened to 20–30 seconds while the time period before concentration measuring was about 40–50 seconds when a conventional reviving method was employed.

First Apparatus Embodiment

Figure 5:
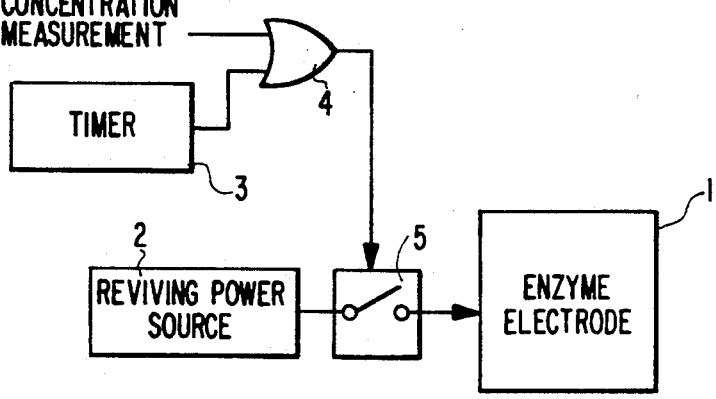
FIG. 5 is a block diagram of an activity maintaining apparatus in accordance with a first apparatus embodiment of the present invention.

FIG. 5 is a block diagram of an activity maintaining apparatus in accordance with a first apparatus embodiment of the present invention.

The activity maintaining apparatus comprises a reviving power source 2 for applying a reviving voltage having a predetermined value to an enzyme electrode 1, a timer 3 for outputting a time-up signal after a time period after application of the reviving voltage to the enzyme electrode i reaches a predetermined time T an OR-gate 4 for receiving an indication signal for concentration measuring and the time-up signal and for outputting an indication signal for applying the reviving voltage to the enzyme electrode 1 and a switch 5 operable based on the indication signal for applying the reviving voltage so as to interconnect the reviving power source 2 and the enzyme electrode 1.

Operation of the activity maintaining apparatus is as follows.

When concentration measuring has not been carried out for a long time period, the time-up signal is supplied to the OR-gate 4 at every time-up operation of the timer 3. The OR-gate 4 outputs the indication signal for applying reviving voltage to the enzyme electrode 1 so as to operate the switch 5 to interconnect the reviving power source 2 and the enzyme electrode 1. Then, the reviving operation for the enzyme electrode 1 is carried out.

When the indication signal for concentration measuring is supplied to the OR-gate 4 before the time-up operation of the timer 3, the OR-gate 4 outputs the indication signal for applying reviving voltage to the enzyme electrode 1 so as to operate the switch 5 to interconnect the reviving power source 2 and the enzyme electrode 1. Then, the reviving operation for the enzyme electrode 1 is also carried out. In this case, a concentration measuring operation is started when the diffusion current decreases to a predetermined threshold value after application of the reviving voltage to the enzyme electrode 1.

In this embodiment also, the enzyme electrode 1 is prevented from reducing its activity too much and a concentration measurement with high accuracy is performed. The time period for awaiting concentration measuring after application of the reviving voltage to the enzyme electrode 1 can be shortened.

Second method Embodiment

Figure 6:
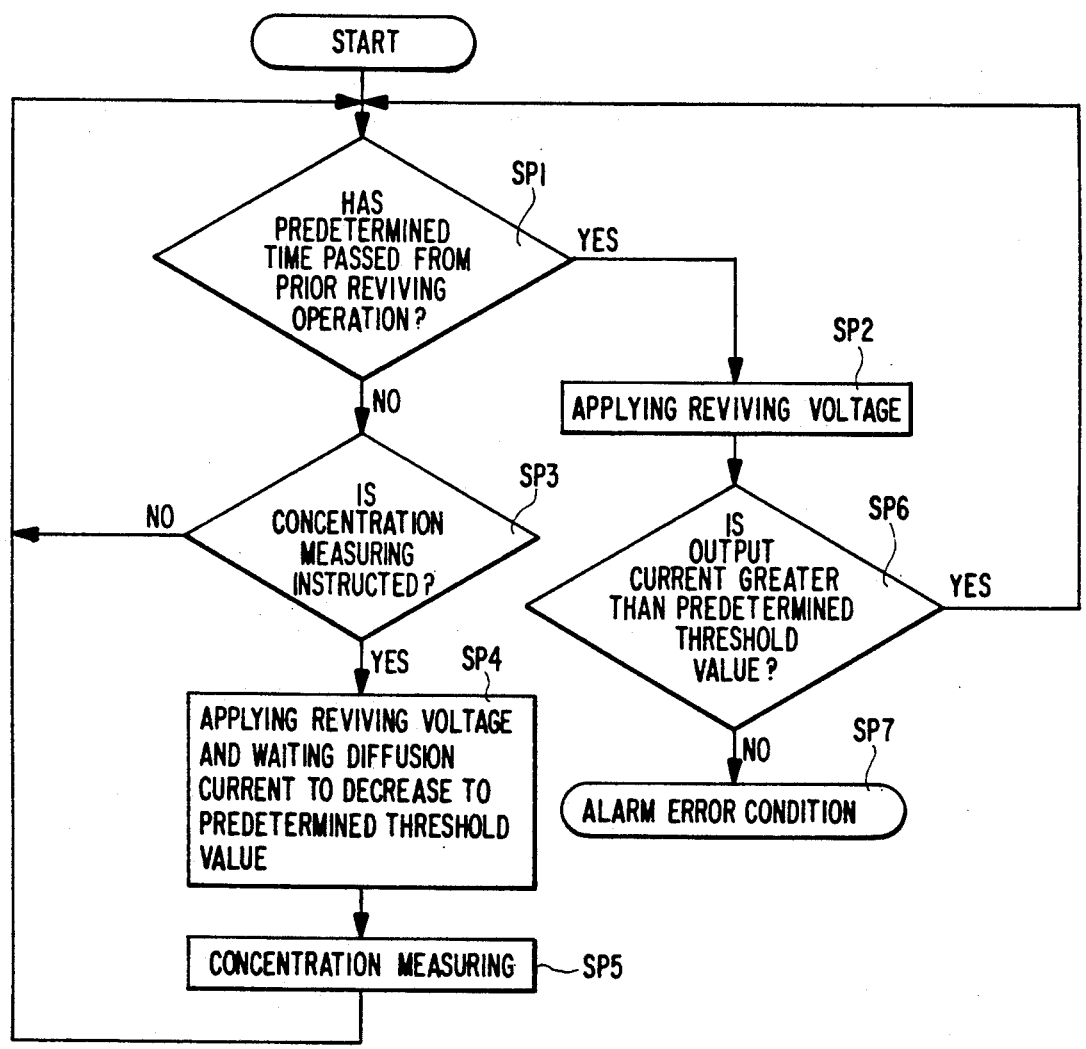
FIG. 6 is a flowchart of an activity maintaining method in accordance with a second method embodiment of the present invention.

FIG. 6 is a flowchart of an activity maintaining method in accordance with a second method embodiment of the present invention.

This method differs from the flowchart shown in FIG. 1 in that additional steps SP6 and SP7 are added after the step SP2 which is shown in FIG. 1. More specifically, after the reviving voltage is applied at every time interval T to the enzyme electrode 1 so as to revive the enzyme electrode 1 in step SP2, it is judged whether or not an output current from the enzyme electrode 1 is greater than a predetermined threshold value in step SP6. When it is judged in step SP6 that the output current is not greater than the predetermined threshold value, the enzyme electrode 1 is determined to be in error and an alarm is output in step SP7. Otherwise, the judgement in step SP1 is carried out again.

When the output current is not greater than the predetermined threshold value after the reviving operation has been performed, the enzyme electrode 1 is in error, i.e. by the breaking of a wire, by disconnection or the like. The enzyme electrode 1 is judged prior to a concentration measuring operation, as to whether or not it is in error based on application of the reviving voltage which is carried out under the condition that a concentration measuring operation is not instructed. The disadvantage with conventional concentration measuring apparatus, which disadvantage is that the enzyme electrode is judged to determine whether or not it is in an error condition only when a concentration measuring operation has been instructed, is overcome by the present invention.

The enzyme electrode 1 may further be judged as to whether or not it is in error based on the application of the reviving voltage to the enzyme electrode due to the instruction for a concentration measuring operation.

Second Apparatus Embodiment

Figure 7:
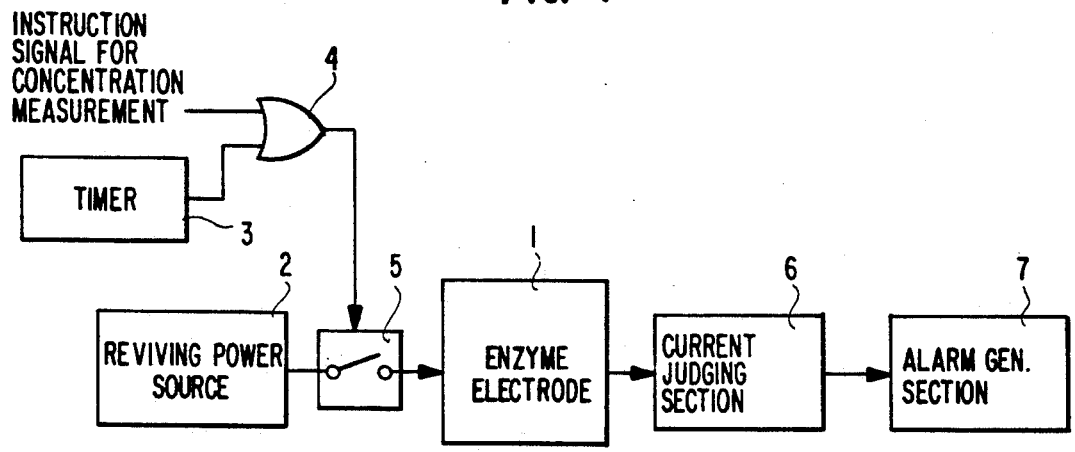
FIG. 7 is a block diagram of an activity maintaining apparatus in accordance with a second apparatus embodiment of the present invention.

FIG. 7 is a block diagram of an activity maintaining apparatus in accordance with a second apparatus embodiment of the present invention.

This apparatus differs from the activity maintaining apparatus shown in FIG. 5 in that the activity maintaining apparatus further comprises a current judging section 6 for judging whether or not the output current output from the enzyme electrode 1 is greater than a predetermined threshold value after a reviving operation is performed, and an alarm generation section 7 for generating an alarm based on the judgement signal output from the current judging section 6, the judgement signal representing that the output current is not greater than the predetermined threshold value.

In this embodiment, after a reviving operation for the enzyme electrode 1 is performed at every predetermined time interval T or at instructing of a concentration measuring, the current judging section 6 judges whether or not the output current output from the enzyme electrode 1 is greater than the predetermined threshold value. Only when it is judged that the output current is not greater than the predetermined threshold value, the alarm generation section 7 operates so as to alarm someone that the enzyme electrode 1 is in error. The enzyme electrode 1 is judged prior to a concentration measuring operation as to whether or not it is in error based on the application of a reviving voltage which is carried out under the condition that a concentration measuring operation is not instructed. The disadvantage with conventional concentration measuring apparatus, which disadvantage is that the enzyme electrode is judged to determine whether or not it is in an error condition only when a concentration measuring operation has been instructed, is overcome by the present invention.

Third Apparatus Embodiment

Figure 8:
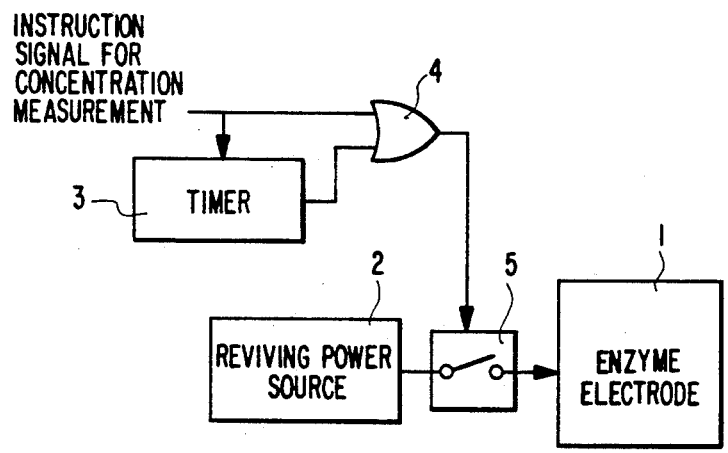
FIG. 8 is a block diagram of an activity maintaining apparatus in accordance with a third apparatus embodiment of the present invention.
Figure 9:
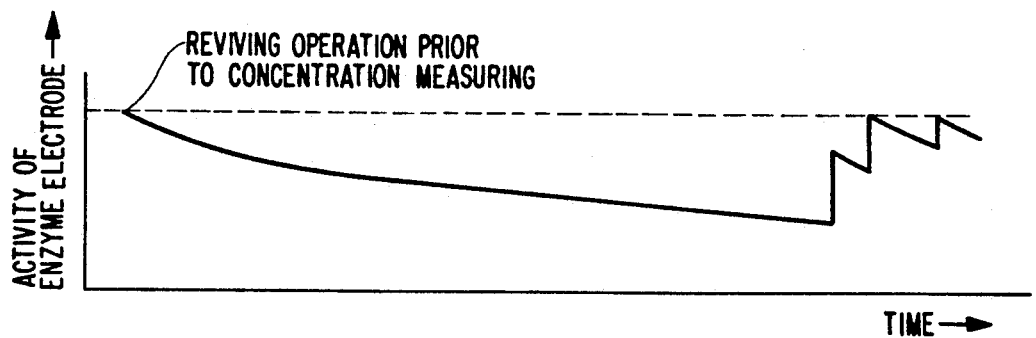
FIG. 9 is a diagram showing variations of the activity of an enzyme electrode to which is applied a conventional reviving method.

FIG. 8 is a block diagram of an activity maintaining apparatus in accordance with a third apparatus embodiment of the present invention.

This apparatus differs from the activity maintaining apparatus shown in FIG. 5 in that the indication signal for concentration measuring is supplied to the timer 3 as a reset signal.

In this embodiment, the timer 3 outputs the time-up signal at every time-up operation when the indication signal for indicating concentration measuring is not applied for a long time. Otherwise, the timer 3 is reset by the indication signal for concentration measuring when the indication signal is applied before the time-up operation of the timer 3 so as to determine the predetermined time interval T not from the application of the reviving voltage due to the time-up signal, but from the application of the reviving voltage due to the instruction signal for concentration measuring. That is the application of the reviving voltage at every predetermined time interval T is carried out by taking into consideration the application of the reviving voltage prior to starting concentration measuring.

This invention is not limited to the foregoing embodiments. Preferably, the time-up signal output from the timer 3 may be supplied to the switch 5 with a predetermined time period delay which corresponds to a time period necessary for a concentration measuring operation.

The terms and expressions which have been employed here are used as terms of description and not of limitations, and there is no intention, in the use of such terms and expressions of excluding equivalents of the features shown and described, or portions thereof, it being recognized that various modifications are possible within the scope of the invention as claimed.

What is claimed is:

1. An apparatus for maintaining activity of an enzyme electrode of a concentration measuring apparatus which measures a concentration of a test substance in a liquid based upon an electrical signal output from said enzyme electrode when an oxidation reaction or a reduction reaction of said test substance is performed on said enzyme electrode, said apparatus comprising:

a reviving power source means for applying a reviving voltage to said enzyme electrode for activating said enzyme electrode, said reviving voltage having a polarity which is reverse with respect to a test voltage which is applied to said enzyme electrode for performing concentration measurement;

connection means for interconnecting said reviving power source means and said enzyme electrode;

interconnection instruction means for providing an interconnection signal for causing interconnection of said reviving power source means and said enzyme electrode in response to either a timing signal indicative of expiration of a predetermined time interval or a signal indicative of an instruction to perform a concentration measurement; and connection controlling means for controlling said connection means to interconnect said reviving power source means and said enzyme electrode in response to an interconnection signal from said interconnection instruction means.

2. An apparatus as set forth in claim 1, further comprising judging means for comparing an electrical signal output from said enzyme electrode and a predetermined threshold value after application of said reviving voltage to said enzyme electrode by said connection means to judge whether or not said enzyme electrode is in an error condition.

3. An apparatus as set forth in claim 2, wherein said judging means judges said enzyme electrode to be in said error condition when an output current from said electrode does not exceed said predetermined threshold value.

* * * * *